United States Patent
Sharrow et al.

(10) Patent No.: US 6,773,418 B1
(45) Date of Patent: Aug. 10, 2004

(54) DEVICE AND METHOD FOR DELIVERY OF AGENTS TO THE FEMALE REPRODUCTIVE TRACT

(75) Inventors: James S. Sharrow, Bloomington, MN (US); Thomas G. Adelman, West Baldwin, ME (US); Frederick J. Foley, Bedford, NH (US)

(73) Assignee: Iotek, Inc., Minneapolis, MN (US)

( * ) Notice: Subject to any disclaimer, the term of this patent is extended or adjusted under 35 U.S.C. 154(b) by 0 days.

(21) Appl. No.: 09/377,012

(22) Filed: Aug. 18, 1999

(51) Int. Cl.$^7$ ................................................. A61M 5/32
(52) U.S. Cl. .................. 604/176; 604/174; 606/119; 606/108; 600/201
(58) Field of Search .................. 604/174, 278, 604/176, 178, 35, 41, 514, 515, 73, 74, 93.01, 104, 75, 275, 279, 523, 181, 264, 21, 285, 327–331, 355; 128/830, 841, 832, 206.24, 207.14, 912, 206.28; 600/34, 35, 201–246; 606/193, 123, 108, 119, 166, 162

(56) References Cited

U.S. PATENT DOCUMENTS

| | | | |
|---|---|---|---|
| 3,534,733 A | | 10/1970 | Phipps et al. |
| 3,608,540 A | * | 9/1971 | Sartorius ................ 128/2 R |
| 3,640,270 A | | 2/1972 | Hoffman |
| 3,786,801 A | * | 1/1974 | Sartorius ................ 128/2 F |
| 3,811,443 A | * | 5/1974 | Dickinson, III et al. .... 128/235 |
| 3,926,192 A | * | 12/1975 | Van Maren ............ 128/303 R |
| 3,952,737 A | * | 4/1976 | Lipfert et al. ............. 128/127 |
| 4,356,989 A | * | 11/1982 | Ireland ................... 248/205.9 |
| 4,474,576 A | | 10/1984 | Gobby |
| 4,543,949 A | * | 10/1985 | Goepp et al. ............. 128/127 |
| 4,601,698 A | | 7/1986 | Moulding, Jr. |

(List continued on next page.)

FOREIGN PATENT DOCUMENTS

| | | |
|---|---|---|
| DE | 19534857 | 11/1996 |
| EP | 0157888 | 10/1985 |
| EP | 0319394 | 6/1989 |
| EP | 0502485 A1 * | 9/1992 |
| FR | 93456 | 4/1969 |
| GB | 1445180 | 8/1976 |
| GB | 1448626 | 9/1976 |

OTHER PUBLICATIONS

Photograph of WISAP Insemination Catheter, Art Nr. 1245A, Char. Nr 913.

(List continued on next page.)

*Primary Examiner*—Brian L. Casler
*Assistant Examiner*—Cris L. Rodriguez
(74) *Attorney, Agent, or Firm*—Shumaker, & Sieffert, PA (57) ABSTRACT

A device and method for delivering an agent to the uterine cervix make use of a seal member that defines a chamber upon engagement with the cervix. An agent delivery port in fluid communication with the chamber is provided for delivery of the agent to the uterine cervix. A vacuum port in fluid communication with the chamber allows application and retention of vacuum pressure to the chamber. At least a portion of the seal member can be made deformable in response to contact with the outer surface of the uterine cervix and application of vacuum pressure. Upon deformation, the seal member substantially seals the chamber against leakage of the agent. The seal member may include a skirt-like member that promotes adhesion of the seal member to the cervix, and enhances the effectiveness of the seal. The device facilitates vacuum application, cervical fixation, and a resulting barrier against uterine fluid leakage, providing an atraumatic, temporary cervical plug that remains effective while the vacuum is applied. In this manner, the device is capable of improving diagnostic or therapeutic effectiveness while reducing waste and expense. The device and method also can be adapted for introduction of surgical or diagnostic instruments, such as ablation catheters or endoscopes.

9 Claims, 10 Drawing Sheets

U.S. PATENT DOCUMENTS

| | | | | |
|---|---|---|---|---|
| 4,606,336 A | * | 8/1986 | Zeluff | 128/130 |
| 4,736,749 A | | 4/1988 | Lundback | |
| 4,770,167 A | * | 9/1988 | Kaali et al. | 128/788 |
| 4,846,819 A | * | 7/1989 | Welch | 604/329 |
| 4,889,533 A | * | 12/1989 | Beecher | 604/330 |
| 5,037,431 A | * | 8/1991 | Summers et al. | 606/131 |
| 5,195,964 A | | 3/1993 | Kletzky et al. | |
| 5,248,304 A | * | 9/1993 | Vigdorchik et al. | 604/278 |
| 5,259,836 A | | 11/1993 | Thurmond et al. | |
| 5,332,802 A | * | 7/1994 | Kelman et al. | 530/356 |
| 5,345,935 A | * | 9/1994 | Hirsch et al. | 600/376 |
| 5,364,375 A | * | 11/1994 | Swor | 604/278 |
| 5,497,771 A | * | 3/1996 | Rosenheimer | 600/323 |
| 5,507,741 A | * | 4/1996 | L'Esperance, Jr. | 606/5 |
| 5,536,243 A | * | 7/1996 | Jeyendran | 600/35 |
| 5,553,612 A | | 9/1996 | Lundback | |
| 5,592,938 A | * | 1/1997 | Scarberry et al. | 128/206.24 |
| 5,647,357 A | * | 7/1997 | Barnett et al. | 128/206.24 |
| 5,676,634 A | * | 10/1997 | Khouri | 600/38 |
| 5,749,845 A | | 5/1998 | Hildebrand et al. | |
| 5,810,840 A | * | 9/1998 | Lindsay | 606/123 |
| 5,816,248 A | | 10/1998 | Anderson et al. | |
| 5,928,249 A | * | 7/1999 | Saadat et al. | 606/119 |
| 5,935,098 A | | 8/1999 | Blaisdell et al. | |
| 5,988,169 A | | 11/1999 | Anderson et al. | |
| 6,059,795 A | * | 5/2000 | Wallace et al. | 606/123 |
| 6,139,538 A | * | 10/2000 | Houghton et al. | 604/515 |
| 6,264,638 B1 | * | 7/2001 | Contente | 604/285 |
| 6,358,226 B1 | * | 3/2002 | Ryan | 604/74 |
| 6,558,314 B1 | * | 5/2003 | Adelman et al. | 600/37 |

OTHER PUBLICATIONS

Urodynamic Balloon Catheter, Catheters and Sets, p. 29, Cook OB/GYN Catalog, Products for Obstetrics, Gynecology & Surgery (1994).

Shapiro Intrauterine Insemination Set, Catheters and Sets, p. 60, Cook OB/GYN Catalog, Products for Obstetrics, Gynecology & Surgery (1994).

Coaxial Catheter Sets, Catheters and Sets, p. 67, Cook OB/GYN Catalog, Products for Obstetrics, Gynecology & Surgery (1994).

TFE Access Sets, Catheters and Sets, p. 74, Cook OB/GYN Catalog, Products for Obstetrics, Gynecology & Surgery (1994).

Werlin–Ishida Coaxial Catheter Set, Catheters and Sets, p. 77, Cook OB/GYN Catalog, Products for Obstetrics, Gynecology & Surgery (1994).

Baggish Aspiration Catheters, Catheters and Sets, p. 84, Cook OB/GYN Catalog, Products for Obstetrics, Gynecology & Surgery (1994).

* cited by examiner

DEVICE AND METHOD FOR DELIVERY OF AGENTS TO THE FEMALE REPRODUCTIVE TRACT

TECHNICAL FIELD

The present invention relates generally to the delivery of agents for medical treatment or diagnosis and, more particularly, to the delivery of such agents to the female reproductive tract.

BACKGROUND

A variety of delivery devices has been developed for the delivery of anesthetics, drugs, irrigation fluids, imaging contrast agents, and other agents to the body. Delivery of such agents can be accomplished either systemically or locally. Systemic delivery generally refers to delivery of agents to the body as a whole. Agents delivered systemically tend to travel to many different areas of the body. Localized delivery generally refers to delivery of agents to a particular area of the body, i.e., on a more targeted basis. There are many methods and techniques for delivering agents to body tissue systemically or locally. Existing techniques include, for example, oral administration, direct injection into body tissue, topical or transcutaneous administration, and intravenous administration.

Systemic delivery has a number of disadvantages. When drugs are systemically administered at high levels, for example, healthy tissue can be harmed, causing serious side effects in some cases. Also, drugs and contrast agents can be expensive, making the delivery of limited dosages more desirable. Systemic delivery may require a higher dosage, however, to achieve a desired level of the agent at the intended site. As a result, a portion of the agent can be wasted, driving up the cost of the treatment or diagnostic procedure. The high cost of pharmaceuticals, contrast agents, and the like makes minimization of waste a significant concern.

The disadvantages of systemic delivery make localized delivery desirable for many applications. One technique for localized delivery is to inject the agent directly into target tissue. Unfortunately, injection requires penetration by a needle or similar device, which is intrusive, painful, and often inaccurate. Moreover, injection may not evenly distribute the agent throughout the target area. To aggravate this situation, several injections may be required for relatively large target areas. Also, injection can produce a high concentration of the agent at the site of the injection, creating a large concentration gradient. Large concentrations are more likely to introduce significant quantities of the agent into the patient's system, undermining the objective of localized delivery.

Transcutaneous delivery is another technique for localized delivery of agents to the body. Transcutaneous delivery systems generally are limited, however, to the application of an agent through the patient's skin or other surface tissue. As a result, transcutaneous delivery of an agent to a target area that is large or situated deep within the patient's body can be difficult. An example of a difficult target area for transcutaneous delivery is cervical and uterine tissue. Typically, a quantity of agent much larger than the amount required at the target site must be applied, resulting in waste and added expense.

SUMMARY

The present invention provides a device for localized delivery of an agent to cervical and/or uterine tissue. The delivery device may include a number of features that aid in reducing leakage of the agent, and thereby improve the efficiency of the device. With more efficient delivery, the device is capable of improving diagnostic or therapeutic effectiveness and reducing waste and expense. In addition, the delivery device can make use of features that facilitate positioning relative to the cervix and cervical fixation without the need for a tenaculum or other painful manipulation devices.

The device may include a seal member that is configured to engage an outer surface of the cervix. Upon engagement with the outer surface of the cervix, the seal member defines a chamber. The seal member further defines a vacuum port and an agent delivery port, both of which are in fluid communication with the chamber.

The seal member can be mounted about an elongated member. The elongated member may take the form of a cannula having a distal end mounted at the agent delivery port. The cannula includes an inner lumen for introduction of an agent delivery catheter through the agent delivery port and into the cervical canal. As an alternative to use of a mounted cannula, a catheter may be introduced directly into the agent delivery port, e.g., via a catheter fitting such as a grommet. The catheter can be guided to the os of the cervical canal for delivery of the agent to the uterus.

The seal member, or a portion thereof, can be made from a compliant material that permits substantial deformation. For example, the seal member can be equipped with a compliant skirt-like member that contacts the outer surface of the cervix. Upon application of vacuum pressure via the vacuum port, at least a portion of the seal member, e.g., the skirt-like member, deforms and substantially seals the outer surface of the cervix against leakage of the agent. In this manner, fluid delivered to the cervix via the agent delivery catheter is substantially retained within the chamber, and more effectively transmitted to the cervix.

The use of vacuum pressure in combination with compliant characteristics of the seal member also facilitate positioning of the device relative to the cervix. In particular, the device permits a firm grasp of the cervix without significant trauma or discomfort. Thus, manipulation of the cervix can be less painful relative to other techniques such as the use of a tenaculum. At the same time, the device can facilitate catheter alignment and insertion for delivery of the desired agent or agents.

The seal member may include inner and outer walls that subdivide the chamber into an outer, annular chamber and an inner, central chamber, which are substantially concentric with one another. In this case, the vacuum port is in fluid communication with the annular chamber, whereas the agent delivery port is in fluid communication with the central chamber. Upon application of vacuum pressure, the inner and outer walls engage the outer surface of the cervix, and serve to separate the annular and central chambers from one another.

In this manner, fluid communication between the vacuum port and the central chamber is substantially avoided, preventing aspiration of the agent delivered via the central chamber by the vacuum port. A plug member that protrudes into the chamber can be further incorporated in the seal member. A catheter can be guided through the plug member. The plug member can be oriented for introduction into the os of the cervical canal, providing an added seal against leakage of agent delivered by the catheter.

Examples of agents that can be delivered using a device in accordance with the present invention include pharmaceutical agents, biological agents, cytotoxic agents, chemotherapeutic agents, hormones, radiotherapeutic agents, anesthetic agents, dyes such as methylene blue, imaging contrast agents, and irrigation fluids. Delivery of such agents using a device constructed as described herein reduces leakage and the resulting costs associated with waste. By preventing significant leakage, the device permits delivery of more precise amounts of an agent in a targeted manner. Moreover, the device can increase and expedite the effectiveness of the agent.

Although the present invention will be described primarily in the context of the delivery of agents in the form of drugs, contrast agents, and the like, the delivery device can be used for the introduction of imaging or surgical devices into the female reproductive tract, i.e., the uterine cervix and uterus. For example, the seal member can be configured to permit introduction of a variety of rigid or flexible devices such as hysteroscopes for endoscopy or ablation procedures within the uterus or cervix. In this case, the agent delivery port can be referred to as an instrument introduction port. Again, the structure of the seal member in combination with the application of vacuum pressure can facilitate the positioning of such devices. Moreover, the delivery device can substantially prevent leakage of distension fluids or other agents used in the course of such procedures.

The present invention provides, in one embodiment, a device for delivery of an agent to the uterine cervix, the device comprising a seal member that defines a chamber upon engagement with the cervix, an agent delivery port in fluid communication with the chamber, and a vacuum port in fluid communication with the chamber, wherein at least a portion of the seal member is deformable in response to application of vacuum pressure via the vacuum port to thereby substantially seal the chamber against leakage of the agent.

In another embodiment, the present invention provides a method for delivering an agent to the uterine cavity, the method comprising inserting a catheter through the cervical canal and into the uterine cavity, engaging a seal member with an outer surface of the cervix to define a chamber, at least a portion of the seal member being compliant, wherein the catheter passes through the seal member, applying vacuum pressure to a vacuum port associated with the chamber such that at least a portion of the seal member deforms to substantially seal the chamber against leakage, and delivering the agent to the uterine cavity via the catheter.

In a further embodiment, the present invention provides a device for delivery of an agent to the uterine cervix, the device comprising a seal member that, upon engagement with the cervix, includes an outer wall and an inner wall that together define an annular chamber and a central chamber substantially concentric within the annular chamber, a vacuum port in fluid communication with the annular chamber, and an agent delivery port in fluid communication with the central chamber, the seal member substantially sealing the central chamber against leakage of the agent upon application of vacuum pressure via the vacuum port.

In an added embodiment, the present invention provides a method for delivery of an agent to the uterine cervix, the method comprising engaging a deformable seal member with the cervix to define a chamber, applying vacuum pressure to the chamber to substantially seal the chamber against leakage, and delivering the agent to the chamber via a port defined in the seal member.

In a further embodiment, the present invention provides a device for introduction of an instrument to a position proximate to the female reproductive tract, the device comprising a seal member that defines a chamber upon engagement with the uterine cervix, an introduction port in communication with the chamber, the introduction port defining an aperture for introduction of an instrument, and a vacuum port in communication with the chamber, wherein at least a portion of the seal member is deformable in response to application of vacuum pressure via the vacuum port to thereby substantially seal the chamber.

In another embodiment, the present invention provides a method for introduction of an instrument to a position proximate to the female reproductive tract, the method comprising engaging a seal member with an outer surface of the uterine cervix to define a chamber, at least a portion of the seal member being compliant, the seal member defining an aperture, inserting an instrument through the aperture defined by the seal member, applying vacuum pressure to a vacuum port associated with the chamber such that at least a portion of the seal member deforms to substantially seal the chamber against leakage, and positioning a distal end of the instrument proximate to the female reproductive tract.

In an additional embodiment, the present invention provides a device for introduction of an instrument to a position proximate a portion of the female reproductive tract, the device comprising a seal member that, upon engagement with the uterine cervix, includes an outer wall and an inner wall that together define an annular chamber and a central chamber substantially concentric within the annular chamber, a vacuum port in fluid communication with the annular chamber, and an instrument introduction port in communication with the central chamber, the seal member substantially sealing the central chamber against the uterine cervix upon application of vacuum pressure via the vacuum port.

In yet another embodiment, the present invention provides a method for introduction of an instrument to a position proximate the female reproductive tract, the method comprising engaging a seal member with the uterine cervix to define a chamber, at least a portion of the seal member being deformable, wherein the seal member defines an aperture, applying vacuum pressure to the chamber to cause deformation of at least the portion of the seal member and substantially seal the chamber against the uterine cervix, introducing an instrument through the aperture defined by the seal member, and positioning a distal end of the instrument proximate to the female reproductive tract.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference numbers and designations in the various drawings indicate like elements.

DETAILED DESCRIPTION

Figure 1:
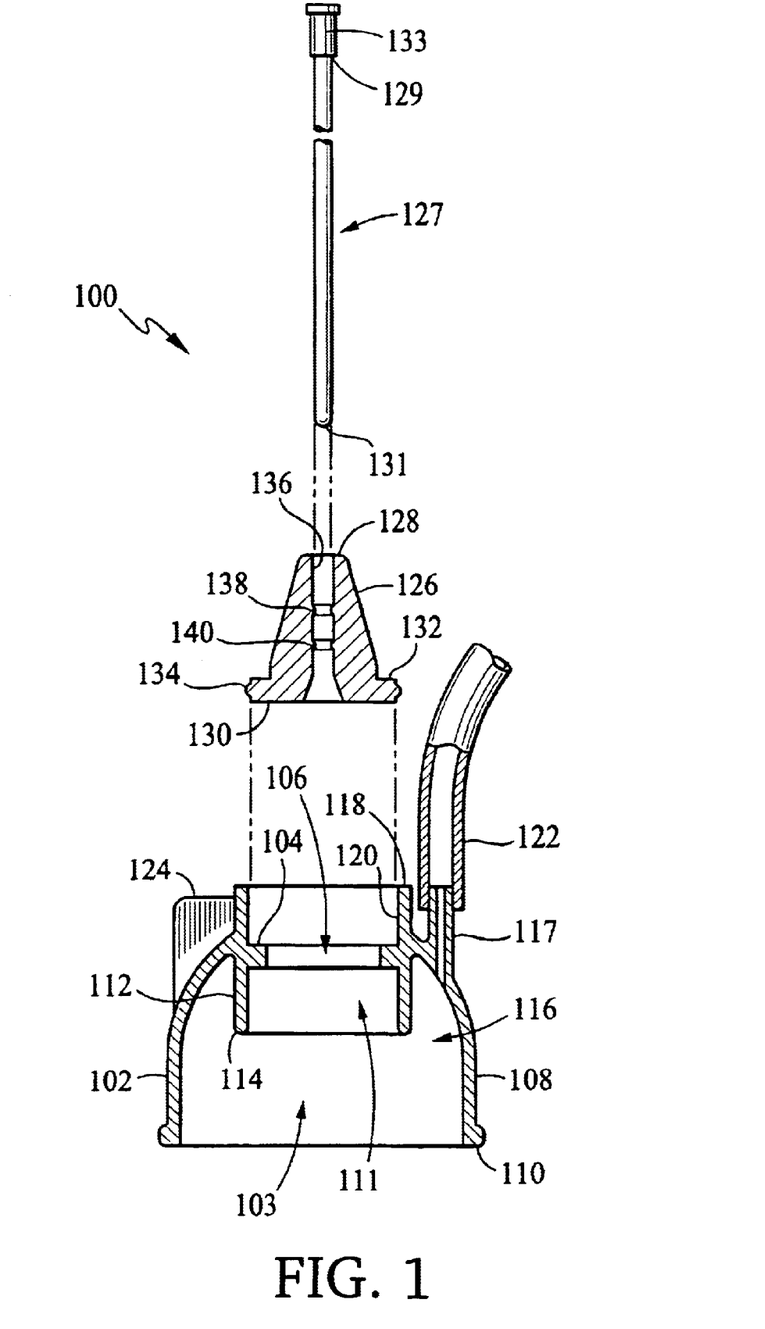
FIG. 1 is an exploded cross-sectional view of an agent delivery device.

FIG. 1 is an exploded cross-sectional view of an agent delivery device 100. As shown in FIG. 1, device 100 may include a seal member having a cup-like member in the form of a vacuum cup 102. Vacuum cup 102 is sized for engagement with an outer surface of the uterine cervix. Upon engagement with the cervix, vacuum cup 102 defines a chamber 103 for delivery of an agent to the female reproductive tract, i.e., the cervix and/or uterus. Cup 102 incorporates a base portion 104 that defines an agent delivery port 106. Agent delivery port 106 provides an aperture for introduction of a cannula or catheter. An outer wall 108 extends from base portion 104 and terminates at an outer rim or outer contact ring 110. An inner wall 112 also extends from base portion 104, circumscribes port 106, and terminates at an inner rim or inner contact ring 114.

The height of inner wall 112 may be approximately half the height of outer wall 108 in the example of FIG. 1. In other embodiments, however, inner wall 112 may have a height that is substantially less than half the height of outer wall 108. Additionally, outer and inner walls 108 and 112 may be generally circular and concentric to one another. Inner wall 112 defines an inner, central chamber 111 for fluid communication with agent delivery port 106 and the source of the agent to be delivered. An outer, annular chamber 116 is defined between inner and outer walls 108 and 112 for fluid communication with a vacuum port 117 and a source of vacuum pressure.

Cup 102 can be formed with a biologically compatible material such as polyethylene, polyurethane, polycarbonate, acetyl butadeine styrene (ABS), or silicone. Thus, in various embodiments, cup 102 can be made from a substantially rigid material or more compliant materials. In some embodiments, however, at least a portion of cup 102 is made from a compliant material. A compliant material may allow outer contact ring 110 to more easily conform to variations in the outer surface of the patient's cervix, and to partially deform upon application of vacuum pressure via vacuum port 117. This feature may contribute to a more robust seal between cup 102 and the outer surface of the uterine cervix.

Device 100 may be suitable for delivery of a variety of agents. An agent can include any type of composition suitable for therapy or diagnosis. Examples include drugs, compositions useful for diagnostic purposes such as dyes or fixatives, genetic material such as DNA, RNA, genes, antisense oligonucleotides, and other antisense material, local anesthetics such as lidocaine, therapeutic agents such as cytotoxic, chemotherapeutic, photosensitive agents, and antiviral agents, adjuvant, penetration enhancers, hormones, and other substances that have medical therapeutic or diagnostic applications. Additionally, the term "agent" can mean an agent in the form of a solution, gel, liquid, or liposome. Although the term is often used in a singular form, it can connote either a single agent or a combination of agents.

With further reference to FIG. 1, a cylindrical flange 118 extends around agent delivery port 106 and extends from base portion 104 in a direction opposite to inner and outer walls 112 and 108. Cylindrical flange 118 has an inner surface 120. Vacuum port 117 extends from outer wall 108 and interconnects with a nozzle of a vacuum line 122. Vacuum port 117 is in fluid communication with annular chamber 116 defined between inner and outer walls 112 and 108. A radially-oriented flange 124 extends between the outer surface of outer wall 108 and the outer surface of cylindrical flange 118. Radially-oriented flange 124 provides a convenient place for a caregiver to grip cup 102 for vaginal introduction into the patient.

Device 100 further may include an elongated member 127 having a proximal end 129 and a distal end 131. A fluid fitting 133 can be mounted at proximal end 129 for introduction of the agent into catheter 127, e.g., using a syringe. For use, cup 102 can be mounted adjacent distal end 131 of elongated member 127. In particular, cup 102 may slidably engage elongated member 127. In this manner, cup 102 can be selectively repositionable along the length of elongated member 127, allowing the care giver to adapt device 100 to particular conditions. In the example of FIG. 1, elongated member 127 takes the form of a catheter. The catheter defines an inner lumen for delivery of an agent. A catheter grommet 126 is mounted at distal end 131 of elongated member 127. Catheter grommet 126 may have a generally conical shape, a proximal end 128, and a distal end 130. The diameter of distal end 130 is greater than the diameter of proximal end 128. A rim 132 is formed around the circumference of distal end 130. At least a portion of the edge of rim 132 has a rib or arcuate profile 134 that extends around the entire circumference of the rim. Distal end 130 of catheter grommet 126 is sized to be inserted into cylindrical flange 118 of vacuum cup 102 such that profile 134 of rim 132 engages inner surface 120 of the cylindrical flange and creates a compression seal therebetween.

Catheter grommet 126 has an inner surface that defines a passage 136 extending between distal and proximal ends 128 and 130. Distal end 130 of passage 136 opposes port 106 in base 104 of cup 102. Two parallel ribs or arcuate profiles 138 and 140 are formed in the inner surface of catheter grommet 126 and extend around the circumference of passage 136. Profiles 138, 140 are axially displaced from one another along the length of passage 136. In the example of FIG. 1, catheter 127 slidably engages catheter grommet 126 and extends through passage 136 and into cup 102. Profiles 138 and 140 engage catheter 127 and create a compression seal between the inner surface of catheter grommet 126 and the catheter. Catheter grommet 126 can be made from a compliant material to permit deformation for insertion into the aperture defined by inner surface 120.

Figure 2A:
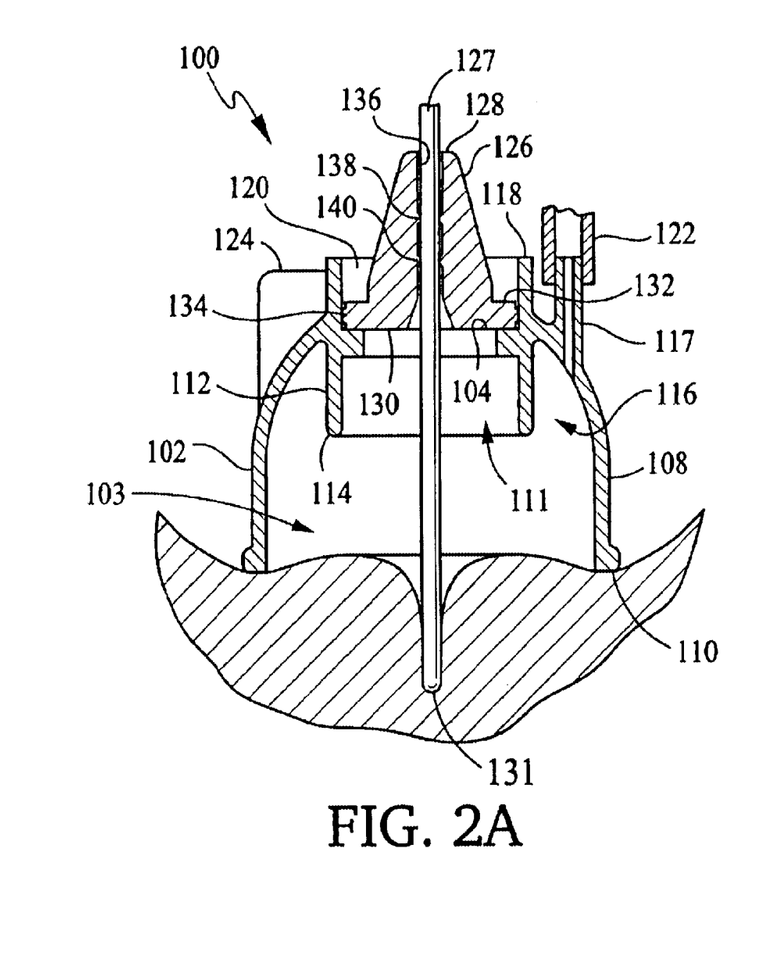
FIG. 2A is a cross-sectional view of an agent delivery device as shown in FIG. 1 in use.

FIG. 2A is a cross-sectional view of an agent delivery device 100 in use. As shown in FIG. 2A, a caregiver estimates the length of the patient's cervical canal and uterine cavity. The caregiver then adjusts the distance between distal end 131 of catheter 127 and distal end 130 of catheter grommet 126 so that the distal end of the catheter will not penetrate into the top portion of the uterine wall when cup 102 engages the patient's cervix. The caregiver then inserts distal end 131 of catheter 127 through the cervical canal until contact ring 110 of outer wall 108 engages the patient's cervix. Air is then withdrawn through vacuum port 117 to create a vacuum in cup 102.

Figure 2B:
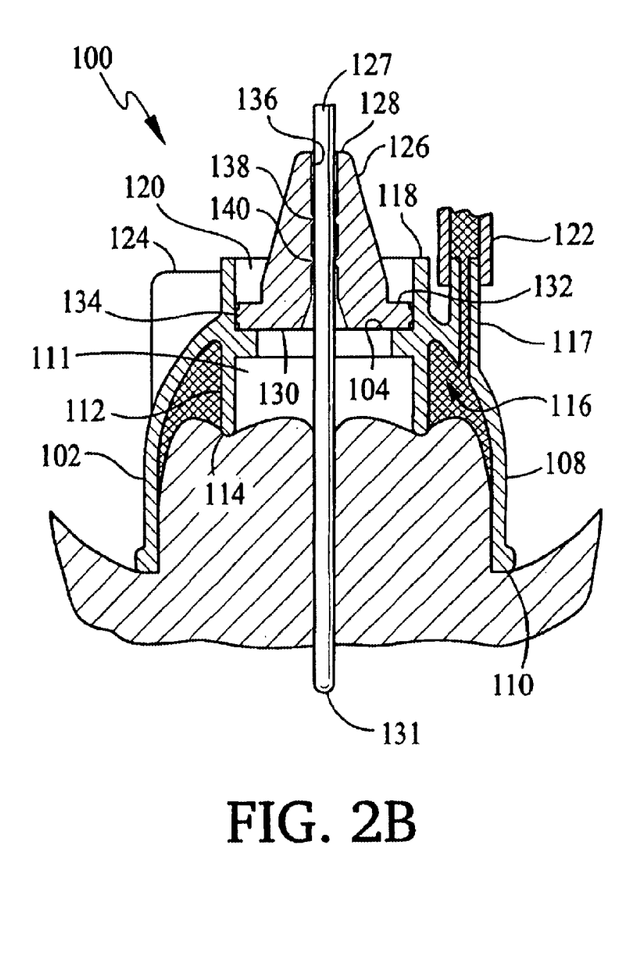
FIG. 2B is a cross-sectional view of an agent delivery device as shown in FIG. 1 illustrating application of vacuum pressure.

FIG. 2B is a cross-sectional view of agent delivery device 100 illustrating application of vacuum pressure. As shown in FIG. 2B, evacuation of chamber 103 causes the tissue of the patient's cervix to be drawn into cup 102 and thereby engage contact ring 114 of inner wall 112. This vacuum also serves to seat cup 102 against the cervix and creates a seal between the cervix and inner and outer contact rings 114 and 110. In particular, the vacuum substantially seals chamber 103 against leakage. In various embodiments, the amount of vacuum pressure that is drawn in cup 102 may be in the range of about −25 to about −600 cm $H_2O$. The amount of vacuum pressure may vary, however, with the diameter, depth, and resulting volume of cup 102, and could be greater. Also, the rate at which the vacuum pressure is applied may be selected to minimize trauma to the cervical tissue, or pain or discomfort to the patient.

In some embodiments, in response to the vacuum pressure, at least a portion of vacuum cup 102 may partially deform to better match the shape and contour of the cervix. After the vacuum is created and inner and outer contact rings 114 and 110 are sealed against the surface of the patient's cervix, the caregiver infuses an agent through catheter 127 and into the uterine cavity. Notably, upon engagement of contact ring 114 with the outer surface of the cervix, chamber 103 provides two separate chambers. Specifically, central chamber 111 and annular chamber 116 are separated from one another by wall 112. Vacuum pressure is applied to annular chamber 116 to provide a seal, whereas central chamber 111 accommodates catheter 127. In this manner, the fluid delivery chamber, i.e., central chamber 111, is separated from the vacuum chamber, i.e., annular chamber 116. Backflow of agent from the uterus is thereby confined to central chamber 111, preventing aspiration of the agent by vacuum port 117.

In some embodiments, the entire uterine cavity can be filled with agent, which permits uniform delivery throughout the uterine wall. The agent then can be passively absorbed into the uterine wall. In other embodiments, an electrode can be positioned on the distal end of the catheter while another electrode is positioned in electrical communication with the patient's body at a point outside the uterine cavity. An electrical current is then conducted between the electrodes to actively transport the agent into the uterine wall. The catheter can include other structures for actively delivering the agent such as ultrasonic transducers, which deliver the agent using principles of phonophoresis. Yet another embodiment may incorporate a heating element at the distal end of the catheter, e.g., for thermal activation of certain agents.

Figure 3A:
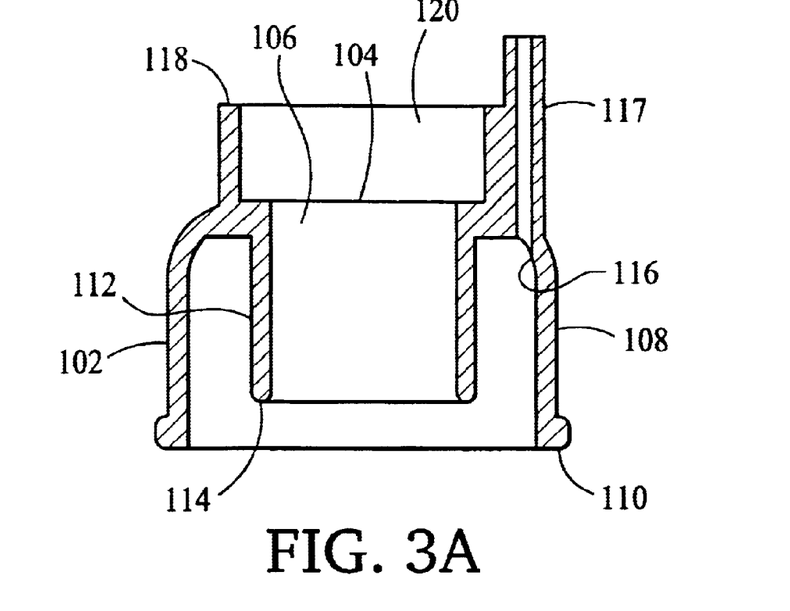
FIG. 3A is a cross-sectional view of a seal member for use with a device as shown in FIG. 1.
Figure 3B:
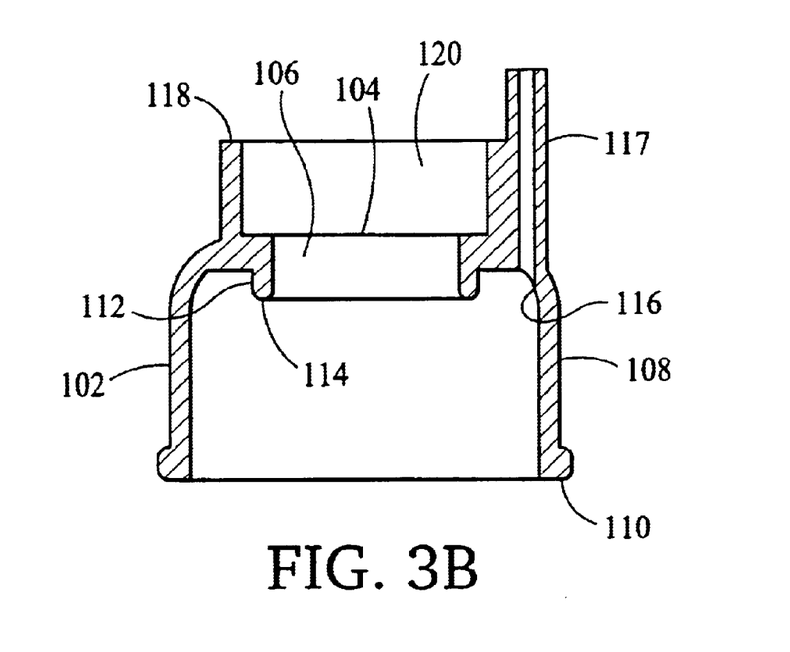
FIG. 3B is a cross-sectional view of another seal member for use with a device as shown in FIG. 1.

FIGS. 3A and 3B are cross-sectional views of vacuum cup 102 with different inner wall heights. As shown in FIGS. 3A and 3B, the height of inner wall 112 can be varied to accommodate different cervical sizes and shapes. For example, in the embodiment shown in FIG. 3A, the height of inner wall 112 is substantially more than half of the height of outer wall 108. In a more specific example, the height of inner wall 112 may be as high as 0.15 inches. This embodiment may be useful for patients that tend to have a flatter cervix.

In another embodiment, as shown in FIG. 3B, the height of inner wall 112 is substantially less than half the height of outer wall 108. In a more specific example, the height of inner wall 112 is between about 0.15 inches and about 0.50 inches. This embodiment may be useful for patients that have a deeper and more conically-shaped cervix. Yet other embodiments may have different proportions between the height of the inner and outer walls 112 and 108, and different diameters for inner and outer contact rings 114 and 110. Furthermore, the overall profile for cup 102 itself can vary. For example, cup 102 could have more of a conical shape or more of a spherical shape.

Figures 4, 5:
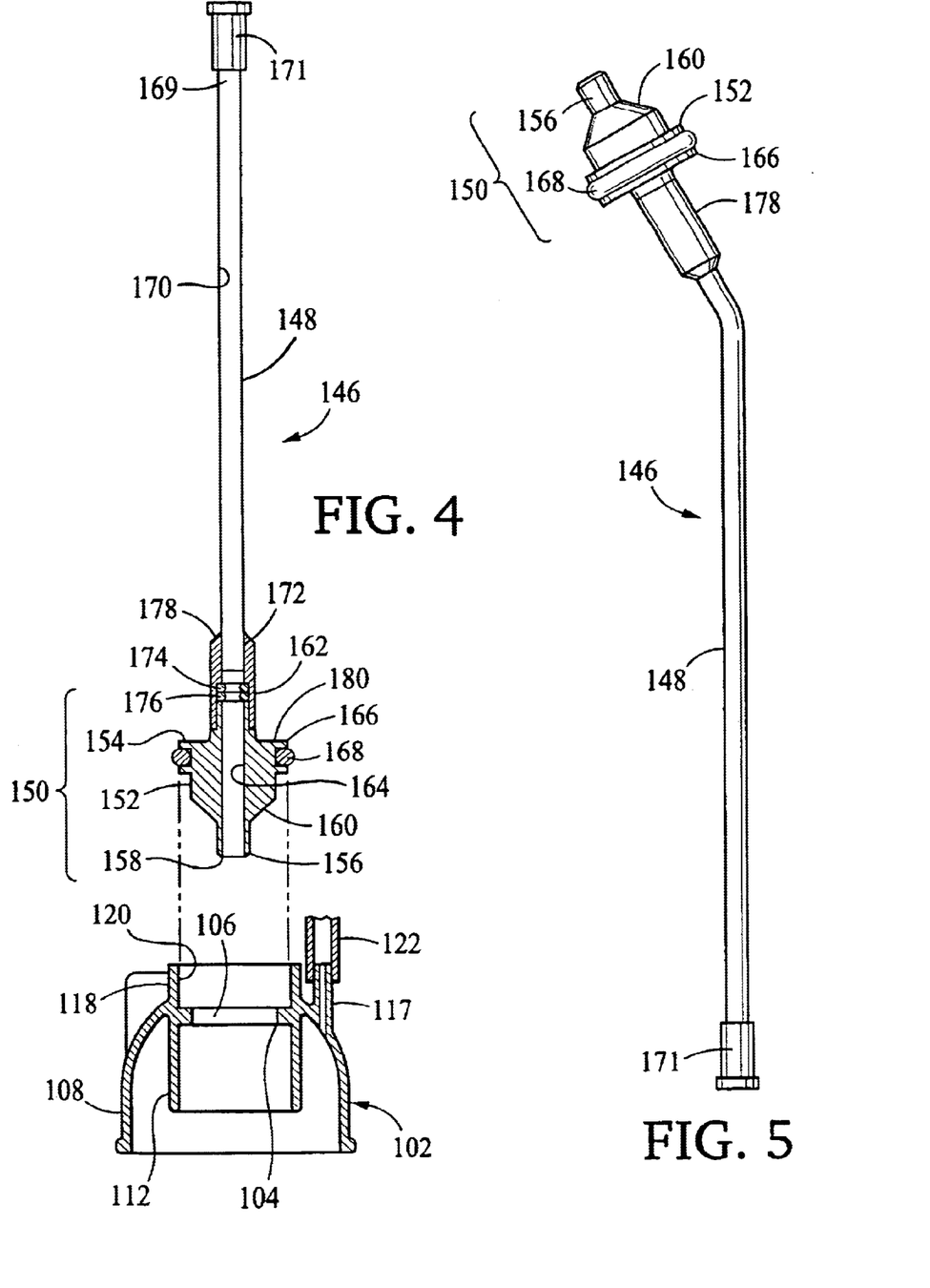
FIG. 4 is an exploded cross-sectional view of another agent delivery device.
FIG. 5 is a side view of an elongated member for use with an agent delivery device as shown in FIG. 4.

FIG. 4 is an exploded cross-sectional view of another agent delivery device 146. Like device 100 of FIG. 1, device 146 includes a seal member incorporating a vacuum cup 102. Again, cup 102 includes a base portion 104 defining agent delivery port 106, inner and outer walls 112 and 108, a cylindrical flange 118, and a vacuum port 117. In contrast to device 100, however, device 146 includes a cannula 148 and cannula grommet 150 instead of catheter grommet 126. Cannula 148 defines an inner lumen 170 sized to accommodate an agent delivery catheter, as will be described. A distal end 169 of cannula 148 may incorporate a fluid fitting 171 for delivery of agents directly within cannula 148. Alternatively, a catheter can be introduced via cannula 148.

As shown in FIG. 4, cannula grommet 150 includes a first cylindrical portion 152 at a proximal end 154, a second cylindrical portion 156 at a distal end 158, and a conical portion 160 extending between first and second cylindrical portions 152 and 156. A neck 162 extends from the proximal end of first cylindrical portion 152. First and second cylindrical portions 152 and 156, conical portion 160, and neck 162 are axially aligned to one another and define a lumen 164 that extends along the axis. A rim 166 extends around the circumference of first cylindrical portion 152, and is positioned adjacent proximal end 154. An o-ring 168 is mounted on rim 166. Rim 166 and o-ring 168 are sized to engage inner surface 120 of cylindrical flange 118 of cup 102 and form a seal therebetween. The diameter of first cylindrical portion 152 of cannula grommet 150 is sized to pass through port 106 of base portion 104 of cup 102.

Cannula 148 defines a lumen 170 and has a distal end 172 opposing neck 162 of cannula grommet 150. O-ring 174 is positioned between distal end 172 of cannula 148 and neck 162. A collar 178 extends around neck 162 of cannula grommet 150, o-ring 174, and distal end 172 of cannula 148. Lumen 170 of the cannula is aligned with lumen 164 of cannula grommet 150. Collar 178 fastens cannula 148 to neck 162 of cannula grommet 150. In one embodiment, the length of cannula 148 is between about four inches and about ten inches. Cannula 148 may be substantially straight. In another embodiment shown in FIG. 5, however, cannula 148 is bent at a position proximal to collar 178. Cannula 148 can be bent at an angle of about 30°, for example, making it easier for the caregiver to handle and position cup 102 relative to the cervix.

The embodiments of device 146 shown in FIGS. 4 and 5 can be used in a manner similar to the embodiment shown in FIG. 1. However, the caregiver can more readily grip cannula 148 to position cup 102 against the patient's cervix. The caregiver then inserts a catheter through the cannula 148 to a delivery position and draws a vacuum in cup 102. In an alternative embodiment, the catheter can be positioned through cannula 148 before cup 102 is positioned against the cervix. In either case, cannula 148 facilitates both manipulation of device 146 and introduction of the agent delivery catheter relative to the cervix. Alternatively, cannula 148 or some other introduction device, e.g., a syringe, could be used with device 146 to simply deliver an agent to the cervix via agent delivery port 106 without the need for catheterization.

Figure 6:
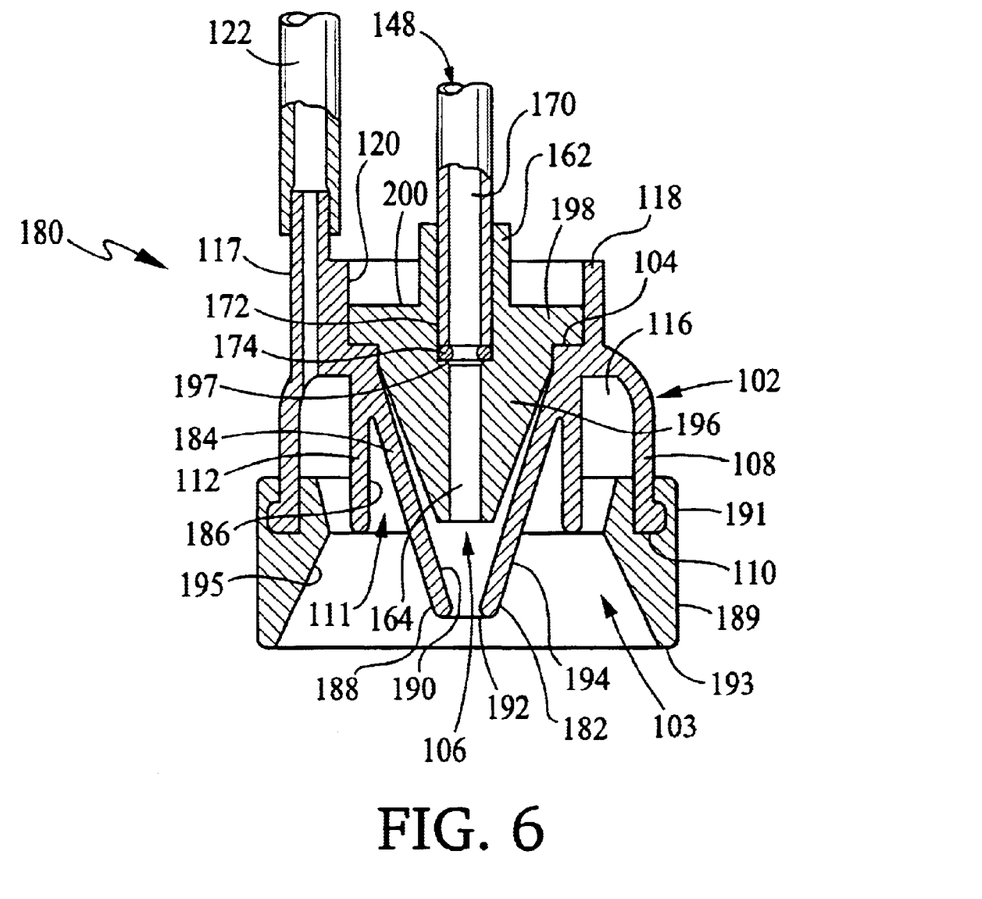
FIG. 6 is a cross-sectional view of an agent delivery device having a seal member with an integrated plug member.

FIG. 6 is a cross-sectional view of an agent delivery device 180 having a cup 102 with a plug member 182. Device 180 is substantially similar to the embodiment shown in FIGS. 3 and 4, and includes cup 102 having a base portion 104, inner and outer walls 112 and 108, and a cylindrical flange 118. Additionally, however, plug member 182 is positioned within inner wall 112. Plug member 182 has a base portion 184 that extends from inner surface 186 of inner wall 112, a tip portion 188 that extends beyond outer contact ring 110, an inner surface 190, and an opening 192 defined in tip portion 188.

Tip portion 188 can be oriented to center a catheter introduced through a cannula 148 within central chamber 111 defined by inner walls 112. Plug member 182 is oriented to engage the cervix proximate to the external os of the cervical canal upon engagement of cup 102 with the cervix. In particular, tip portion 188 engages the os of the cervical canal, providing an added seal against leakage of agent introduced into the uterus. Thus, plug member 182 protrudes from cup 102 and into chamber 103. Agent delivery port 106 extends through plug member 182.

Figure 7:
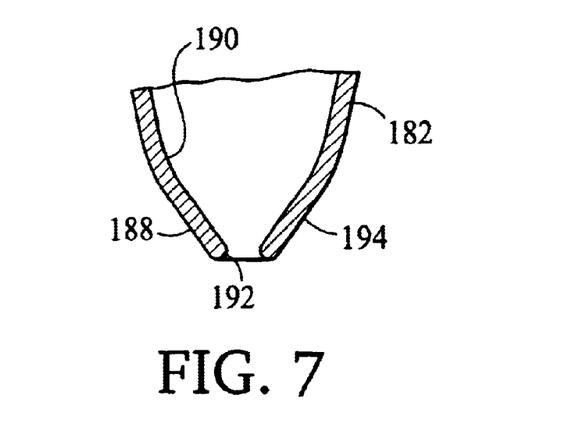
FIG. 7 is a cross-sectional view of a plug member for use with a device as shown in FIG. 6.

Plug member 182 can have a variety of different shapes. In one example, plug member 182 has a conical shape with a substantially straight surface 194. In another example, as shown in FIG. 7, surface 194 of plug member 182 is slightly curved to give it an acorn-shaped profile. Plug member 182 preferably is integrally formed with cup 102, e.g., by injection molding. Alternatively, plug member 182 could be bonded to cup 102, e.g., by adhesive, thermal, or ultrasonic bonding techniques.

Although plug member 182 is illustrated with a cup 102 having central chamber 111 and outer chamber 116, it could be used with a single-chamber cup. In this case, plug member 182 could be engaged within the cervical os to augment the seal provided by cup 102 and chamber 103. In some applications, the use of a single chamber cup 102 with plug member 182 may be effective. However, incorporation of inner and outer chambers 111, 116 is generally preferred.

Delivery device 180 further includes an annular skirt 189. Together, cup 102 and skirt 189 form the seal member. Annular skirt 189 has a base portion 191 that is attached to outer contact ring 110. Annular skirt 189 extends out to a rim 193 that can be made thinner than base portion 191. Annular skirt 189 is formed from a compliant material and will substantially conform to the outer surface of the patient's cervix, improving the seal achieved by cup 102. In a preferred embodiment, skirt 189 is insert molded over ring 110 of cup 102, thereby coupling the skirt to the cup to provide a generally integral construction. Skirt 189 can be bonded to cup 102 using other techniques, however, such as adhesive, thermal, or ultrasonic bonding techniques.

In one embodiment, the material forming the annular skirt 189 has enough compliance so that rim 193 will fan out and at least a portion of inner surface 195 of annular skirt 189 will lay against the surface of the patient's cervix. Examples of materials that can be used to form annular skirt 189 include a variety of biocompatible silicone gel materials or low durometer silicone. A suitable silicone material may have a hardness, for example, in the range of 5 to 30 Shore A. An example of one suitable silicone gel material is MED 6340, commercially available from NUSIL Silicone Technologies, of Carpinteria, Calif. The MED 6340 silicone gel is tacky and exhibits a hardness characteristic such that a 19.5 gram shaft with a 6.35 mm diameter has been observed to penetrate the gel approximately 5 mm in approximately 5 seconds. This hardness characteristic is not a requirement, but merely representative of that exhibited by the commercially available MED 6340 material.

Device 180 also may include a cannula grommet 196 similar to cannula grommet 150 shown in FIGS. 4 and 5, but generally conical in shape. Cannula grommet 196 can be sized to pass through port 106 in base portion 104 and generally conform to inner surface 190 of plug member 182. A rim 198 extends from a proximal portion 200 of cannula grommet 196 and is sized to engage inner surface 120 of cylindrical flange 118 on cup 102. A neck 162 extends from the proximal portion of cannula grommet 196. Cannula grommet 196 has an inner surface that defines a lumen 164. The inner surface has a radial portion 197. An o-ring 174 can be seated against radial portion 197 of the inner surface. A distal end 172 of cannula 148 is inserted into lumen 164 of cannula grommet 196 and adjacent o-ring 174. Lumen 170 of cannula 148 is aligned with and in fluid communication with lumen 164 of cannula grommet 196. Lumens 164, 170 may accommodate an agent delivery catheter.

Figure 8A:
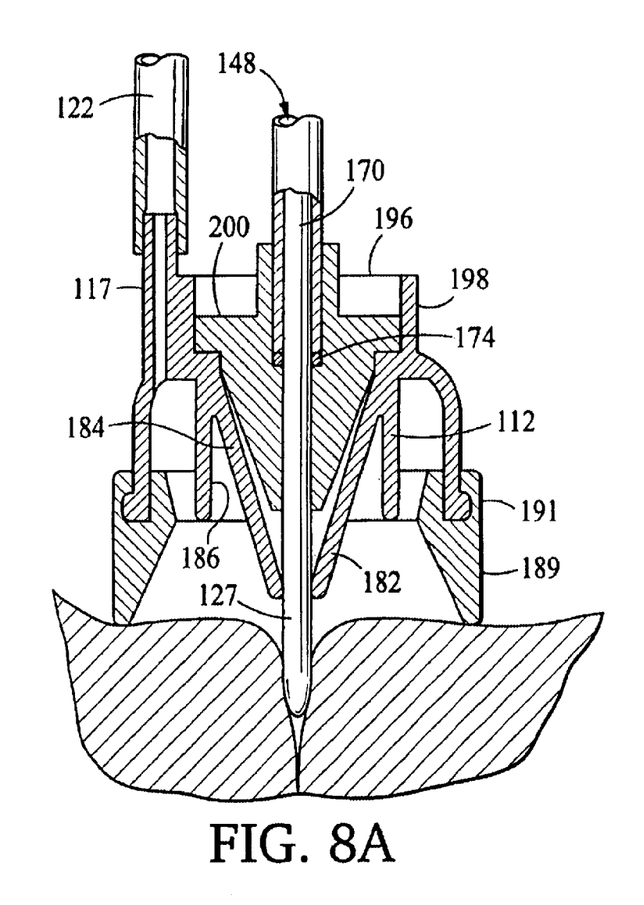
FIG. 8A is a cross-sectional view of an agent delivery device as shown in FIG. 6 in use.
Figure 8B:
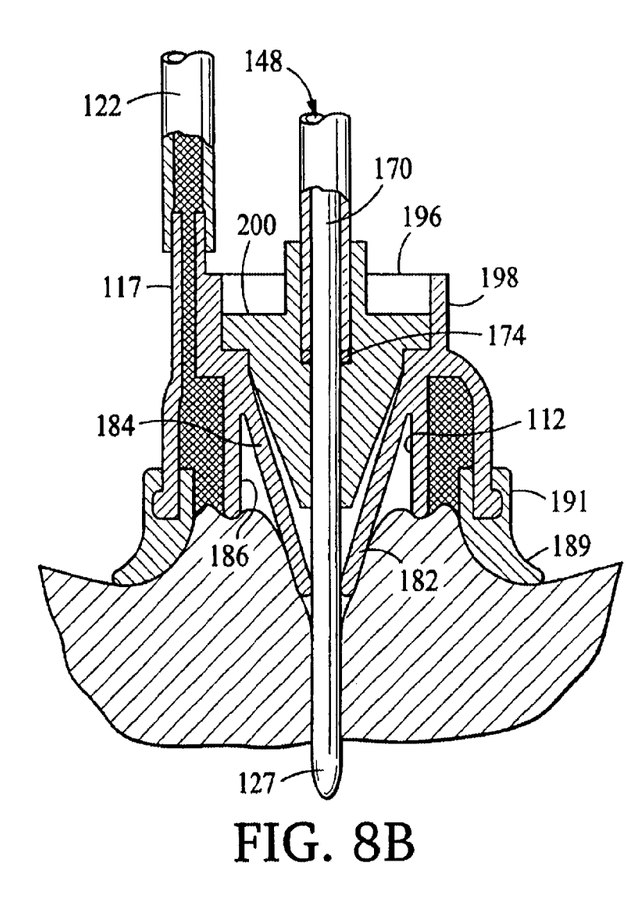
FIG. 8B is a cross-sectional view of an agent delivery device as shown in FIG. 6 illustrating application of vacuum pressure.

In use, cup 102 of device 180 is positioned against the cervix in a manner similar to the embodiment shown in FIGS. 2A and 2B. However, tip portion 188 of plug member 182 is inserted into or to a point proximate to the os of the cervical canal, which adds an additional seal directly at the os and cervical canal. As shown in FIG. 8A, for example, annular skirt 189 is positioned in contact with the outer surface of the cervix. A catheter 127 is translated through cannula 148 and into the os of the cervix. Upon application of vacuum pressure, as shown in FIG. 8B, plug member 182 is drawn into the os of the cervical canal. At the same time, inner wall 112 is drawn into contact with the outer surface of the cervix. The compliant skirt 189 compresses and deforms upon application of the vacuum pressure, to permit inner wall 112 to engage the outer surface of the cervix, and enhance the resulting seal.

Figure 9:
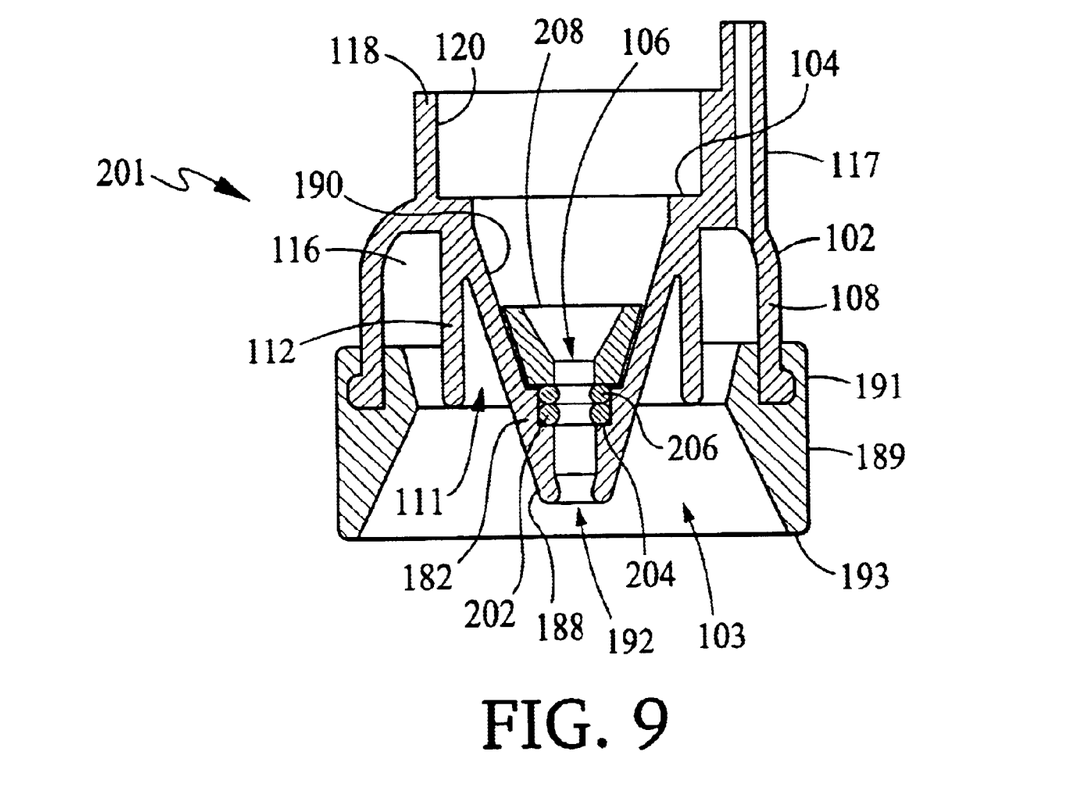
FIG. 9 is a cross-sectional view of a device having an alternative plug arrangement.

FIG. 9 is a cross-sectional view of an agent delivery device, generally shown as 201, having an alternative plug arrangement. Device 201 is substantially similar to the embodiment shown in FIG. 6. Cup 102 includes, for example, inner and outer walls 112 and 108, a base portion 104, a cylindrical flange 118, and a plug member 182. Additionally, inner surface 190 of plug member 182 defines a radially-oriented surface 202, and two o-rings 204 and 206, which are seated against radially-oriented surface 202. O-rings 204 and 206 are held in place by an annular member 208. This embodiment is used in a manner similar to the embodiment shown in FIG. 1. However, the catheter can be passed directly through agent delivery port 106 in base portion 104, through o-rings 204 and 206, and out opening 192 at the tip of plug member 182. O-rings 204 and 206 seal any gaps between cup 102 and the catheter. Hence, a grommet is generally unnecessary in the embodiment of FIG. 9, but could be incorporated along with a cannula if desired.

Figure 10A:
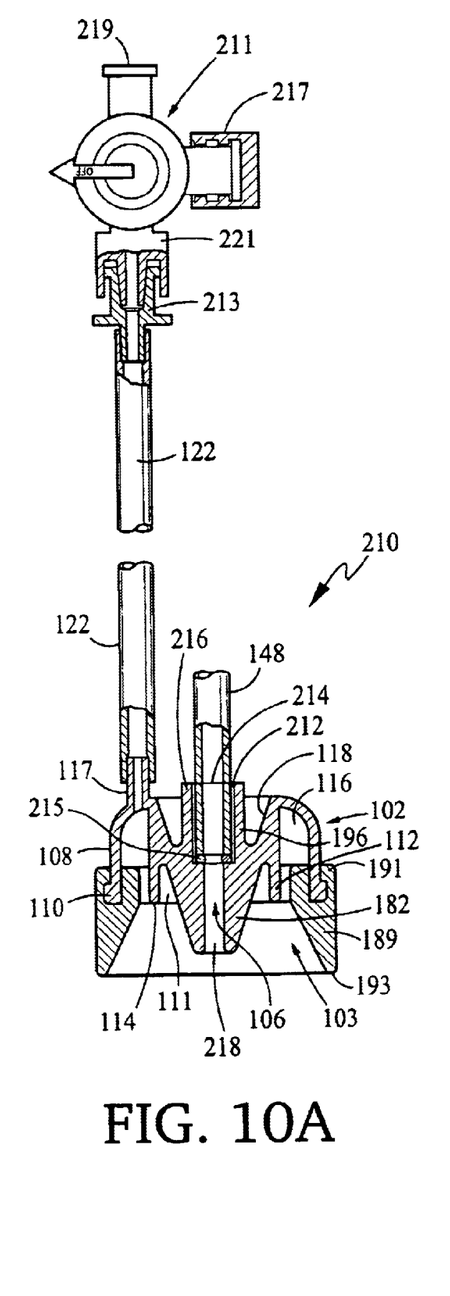
FIG. 10A is a cross-sectional view of another agent delivery device having an integrated plug member.

FIG. 10A is a cross-sectional view of another agent delivery device 210 having a cup 102 with a plug member 182. Device 210 conforms substantially to device 180 of FIG. 6. For example, agent delivery device 210 includes a seal member formed by cup 102, skirt 189, agent delivery port 106, and vacuum port 117. In contrast to device 180, however, device 210 makes use of a one-piece construction in which both plug member 182 and a cannula receptacle 212 are integrally formed with cup 102, e.g., by injection molding. FIG. 10A further illustrates the connection of a vacuum line 122 between vacuum port 117 and a four-way stopcock 211 that can be connected to vacuum pump. Stopcock 211 is coupled to vacuum line 122 via a connector 213. In particular, a first inlet 221 engages connector 213. Outlet 217 communicates with a remote vacuum pump and first inlet 221. A second inlet 219 permits inflow of air to release the vacuum applied to chamber 103.

As shown in FIG. 10A, cannula receptacle 212 defines a cylindrical first bore 214, formed by wall 216. In the example of FIG. 10A, first bore 214 is sized to receive a cannula 148, and can be bonded to the cannula. First bore 214 also may incorporate one or more o-rings 215 for receipt of a catheter, either directly or via cannula 148. In either case, bore 214 terminates at a proximal portion of plug member 182, at which point the plug member defines a second bore 218. Second bore 218 has a diameter sized to accommodate a catheter for introduction into the cervical canal. Together, bores 214, 218 and o-ring 215 define agent delivery port 106 for accommodation of an agent delivery catheter.

Figure 10B:
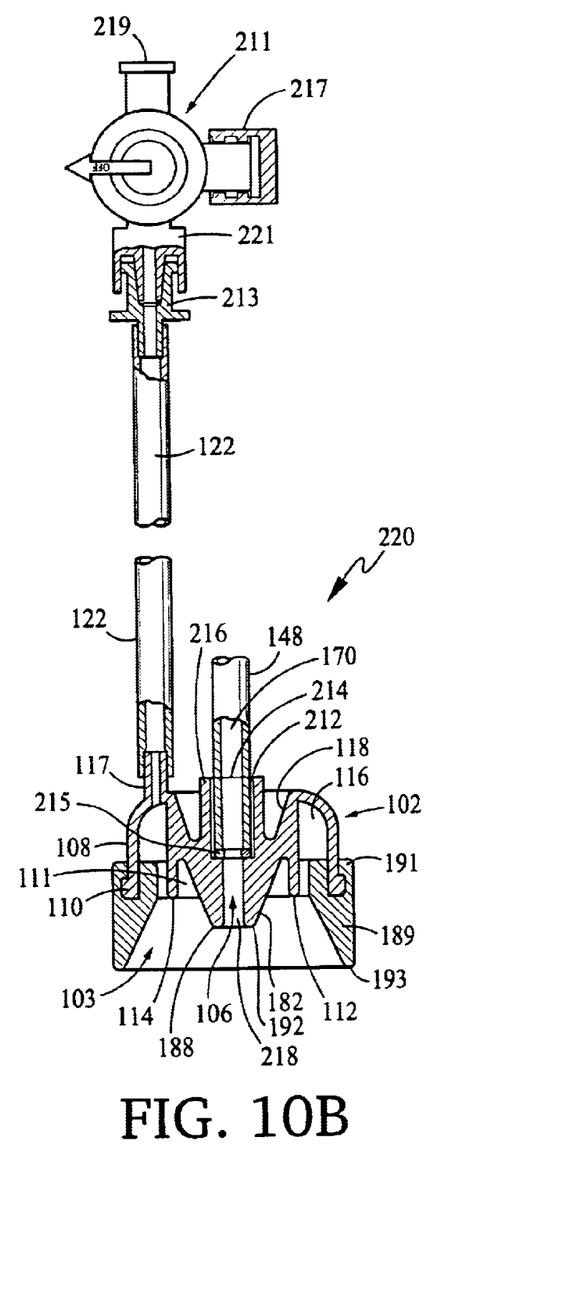
FIG. 10B is a cross-sectional view of a device as shown in FIG. 10A with an integrated plug member having an alternative depth.

FIG. 10B is a cross-sectional view of an agent delivery device 220 that conforms substantially to that shown in FIG. 10A, but which incorporates an integrated plug member 182 having an alternative height. In the embodiment of FIG. 10A, for example, plug member 182 has a height, extending from a proximal portion of skirt 189, that is substantially more than half of the height of the skirt. In the example of FIG. 10B, the height of plug member 182 is substantially less than half of the height of skirt 191. In particular, in the example of FIG. 10A, the height of plug member 182 is between about 5.4 and about 6.4 mm. In the example of FIG. 10B, the height of plug member 182 is between about 2.8 and about 3.8 mm.

Figure 10C:
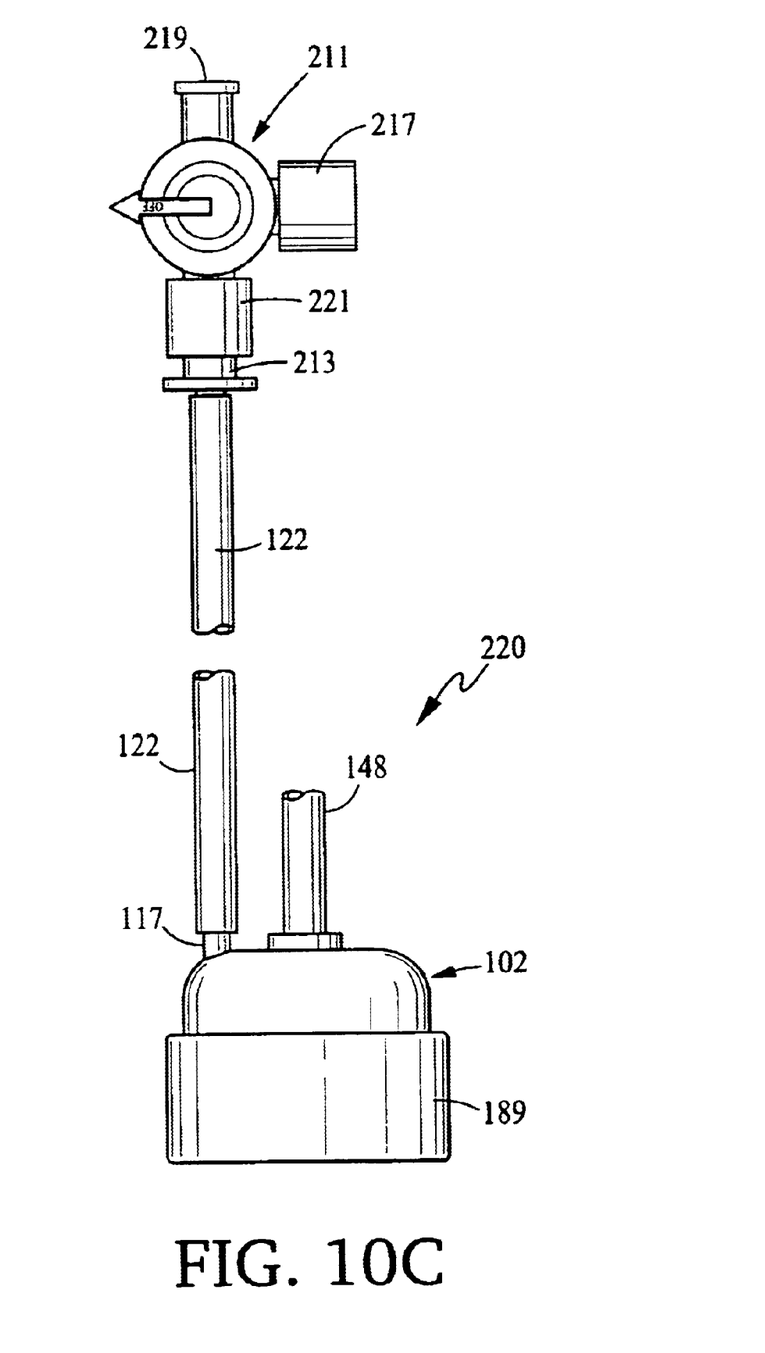
FIG. 10C is an exterior view of an agent delivery device as shown in FIG. 10B.

The embodiment of FIG. 10B may be more suitable for a patient with a flatter cervix, whereas the embodiment of FIG. 10A may be more suitable for a patient with a deeper and more conically-shaped cervix. In operation, device 210, 220 as shown in FIG. 10A or 10B can be used substantially in the manner shown in FIGS. 8A and 8B. In particular, vacuum pressure can be applied to cup 102 to form a first seal, while plug member 182 is engaged with the os of the cervical canal to form a second seal. FIG. 10C is an exterior view of an agent delivery device as shown in FIG. 10B.

Figure 11:
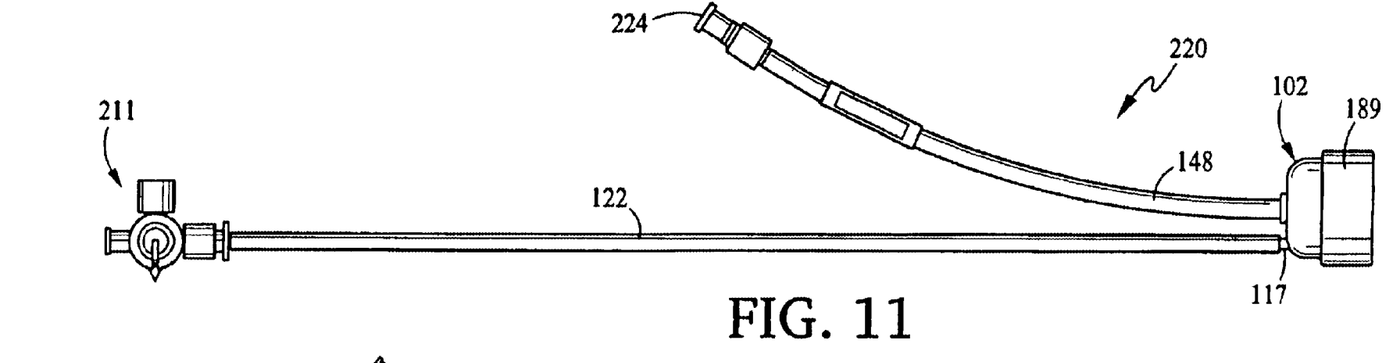
FIG. 11 is another view of an agent delivery device as shown in FIGS. 10A, 10B, and 10C coupled to a cannula and vacuum line.

FIG. 11 is another view of an agent delivery device 220 as shown in FIGS. 10A, 10B, and 10C coupled to a cannula 148 and vacuum line 122. Cannula 148 may include a introduction port 224 for receipt of agent delivery catheters, surgical catheters, diagnostic catheters and the like. For example, cannula 148 may accommodate a hysteroscope providing a laser or thermal ablation catheter for surgery or an endoscope for imaging. Such catheters may include multiple lumens, e.g., for agent delivery, imaging, and surgery. Incorporation of other surgical or diagnostic instruments are conceivable.

Figure 12:
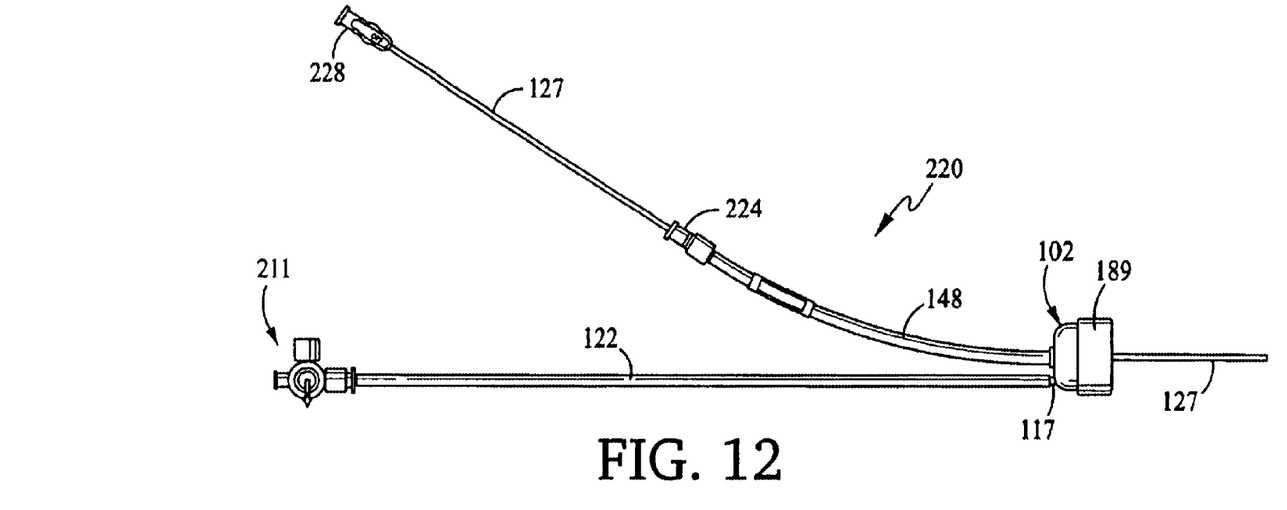
FIG. 12 is a view of the agent delivery device of FIG. 11 illustrating introduction of a catheter.

FIG. 12 is a view of the agent delivery device 220 of FIG. 11 illustrating introduction of a catheter 127. As shown in FIG. 12, catheter 127 is introduced via an inner lumen defined by cannula 148 and through cup 102. A proximal end of catheter 127 can be fitted with a luer lock injection port 228 by which a caregiver may inject an agent into the catheter.

A number of embodiments of the present invention have been described. Nevertheless, it will be understood that various modifications may be made without departing from the spirit and scope of the invention. Accordingly, other embodiments are within the scope of the following claims.

What is claimed is:

1. A medical device comprising:

a deformable seal member defining a chamber; and a vacuum port in fluid communication with the chamber, wherein the seal member includes a compliant and tacky gel material that interfaces with a body organ during use, and wherein the seal member includes a cup member and a skirt member that extends outward from a convex side of the cup member, wherein the cup member is formed from a substantially rigid polymeric material and the skirt member is formed from a compliant and tacky silicone gel material.

2. The medical device of claim 1, wherein the skirt member is coupled to the cup member by one of insert molding, adhesive bonding, thermal bonding and ultrasonic bonding.

3. The medical device of claim 1, wherein the skirt member is deformable in response to application of vacuum pressure via the vacuum port to thereby substantially seal the chamber.

4. The medical device of claim 1, further comprising an introduction port in communication with the chamber, the introduction port defining an aperture for introduction of an instrument.

5. A medical device comprising:

a seal member defining a chamber, the seal member including a cup member formed from a substantially rigid polymeric material and a skirt member coupled to the cup member, the skirt member including a compliant and tacky material;

a vacuum port in fluid communication with the chamber; and an introduction port in communication with the chamber, the introduction port defining an aperture for introduction of an instrument, wherein the skirt member is deformable in response to application of vacuum pressure via the vacuum port to thereby substantially seal the chamber.

6. The medical device of claim 5, wherein the skirt member extends outward from a convex side of the cup member.

7. The medical device of claim 5, wherein the skirt member includes a compliant and tacky gel material.

8. The medical device of claim 5, wherein the skirt member includes a compliant and tacky silicone gel material.

9. The medical device of claim 5, wherein the skirt member is coupled to the cup member by One of insert molding, adhesive bonding, thermal bonding and ultrasonic bonding.

* * * * *